United States Patent [19]

Baier

[11] Patent Number: 5,013,294
[45] Date of Patent: May 7, 1991

[54] INSUFFLATION DEVICE FOR ENDOSCOPIC INTERVENTION

[75] Inventor: Manfred Baier, Bretten, Fed. Rep. of Germany

[73] Assignee: Richard Wolf GmbH, Fed. Rep. of Germany

[21] Appl. No.: 272,315

[22] Filed: Nov. 17, 1988

[30] Foreign Application Priority Data

Nov. 17, 1987 [DE] Fed. Rep. of Germany ....... 3739003

[51] Int. Cl.$^5$ ............................................. A61M 13/00
[52] U.S. Cl. ..................................... 604/26; 128/747; 128/748
[58] Field of Search ....................... 604/23, 26, 57, 65, 604/67, 118, 246; 128/747, 748, 4

[56] References Cited

U.S. PATENT DOCUMENTS

| | | | |
|---|---|---|---|
| 3,674,010 | 7/1972 | Falenks | 128/747 |
| 3,870,072 | 3/1975 | Lindemann | 604/26 |
| 3,982,533 | 9/1976 | Wiest | 604/26 |
| 4,048,992 | 9/1977 | Lindemann et al. | 604/26 |
| 4,207,887 | 6/1980 | Hiltebrandt et al. | 604/26 |
| 4,464,169 | 8/1984 | Semm | 604/26 |
| 4,676,774 | 6/1982 | Semm et al. | 604/26 |
| 4,874,362 | 10/1989 | Wiest et al. | 604/26 |

FOREIGN PATENT DOCUMENTS 2733650 2/1979 Fed. Rep. of Germany ...... 128/747

Primary Examiner—Randall L. Green
Assistant Examiner—K. M. Reichle
Attorney, Agent, or Firm—Hill, Van Santen, Steadman & Simpson

[57] ABSTRACT

An insufflation device for filling a body cavity, such as an abdominal cavity, with a gas from a gas bottle via an expansion valve and a feed pipe leading to the body cavity characterized by the feed pipe being formed along in length by two channels with the first of the two channels having an expansion valve for setting an over-pressure for rapid filling of the body cavity during an initial period and the second channel having an expansion valve to adjust the pressure to the pressure desired in the body cavity. The pressure of the second flow is monitored and compared by an electronic evaluator system, which will interrupt the flow and sound alarms if the pressure exceeds a predetermined amount over the desired value and also if the pressure exceeds a predetermined maximum amount.

7 Claims, 1 Drawing Sheet

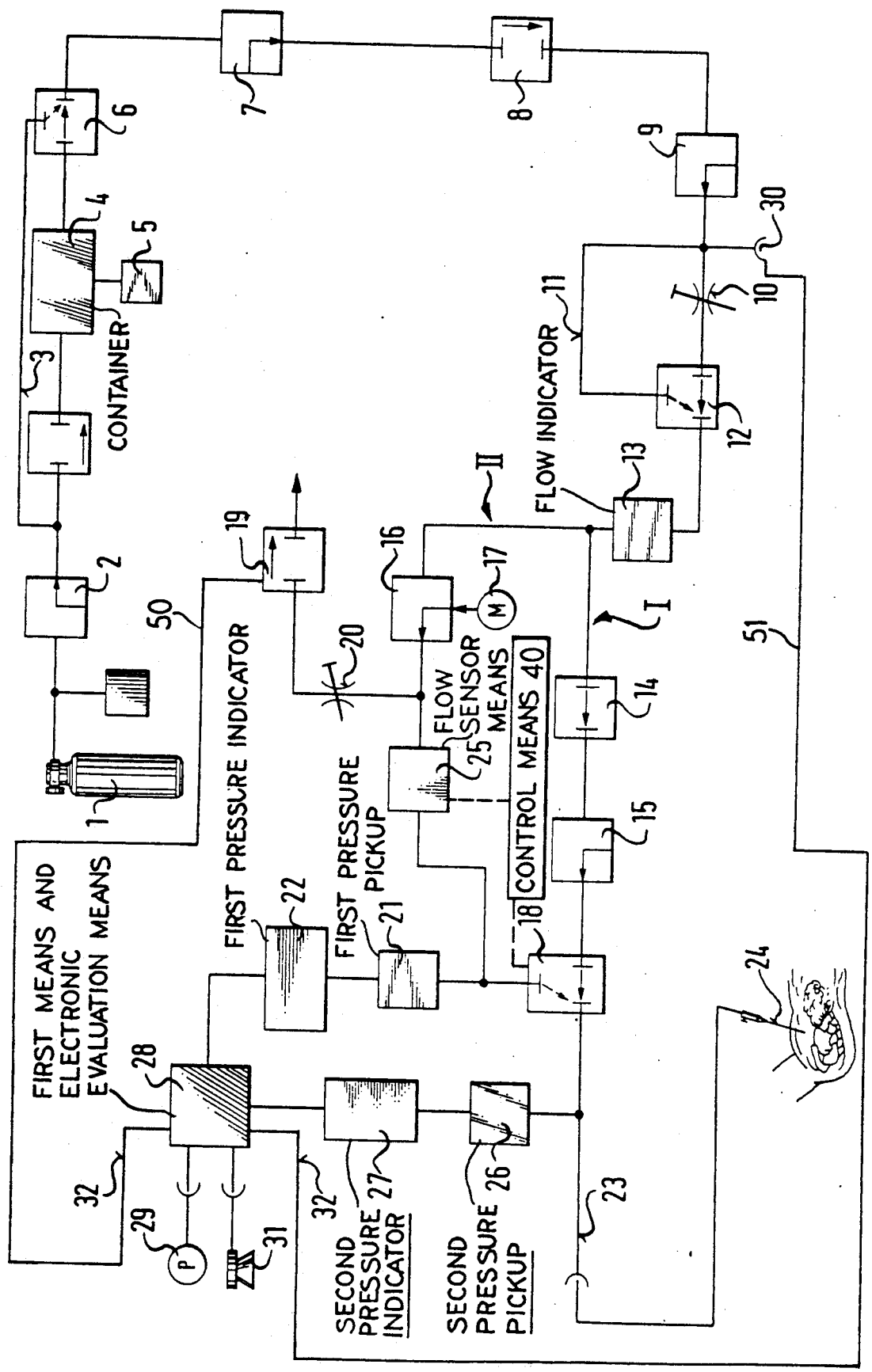

INSUFFLATION DEVICE FOR ENDOSCOPIC INTERVENTION

BACKGROUND OF THE INVENTION

The present invention relates to an insufflation device for endoscopic interventions.

Upon performing endoscopic interventions in animal or human body cavities, it is necessary, for example, in the case of a laparoscopic intervention, to lift the abdominal integument off the internal organs by insufflation of an appropriate gas, so that an unobstructed space is thereby produced for the instruments, which are to be introduced into the abdominal space. In order that a constant pressure, as possible, may be obtained in the body cavity during the intervention, use is made, for example, of an insufflation device according to the German Patent specification No. 30 00 218. In the case of this device, the gas is fed into the body cavity from a gas container, via an intermediate container, an expansion valve, a shut-off valve, a pressure gauge and a flow indicator, and a feed pipe with a cannula which transpierces the abdominal integument.

If other supplemental devices are utilized in the known insufflation systems, excessive pressure may arise very quickly in the body cavity in particular circumstances. These excessive pressures can be caused by faulty operation or handling. These excessive pressures may represent a considerable risk to the patient. Protection against such unacceptable increases or rises in the pressure beyond a specified level is either not available in the known insufflation devices or is only available to an adequate extent.

Another disadvantage of the known insufflation devices is that a pressure drop within the body cavity, as a result of incurring a loss of gas, is detected and made up by the system only after a definite bottom threshold value was reached. The pressure is not kept constant in the abdominal cavity, but is merely maintained to an insufficient degree and continuously fluctuates back and forth between the upper and lower limiting values.

In addition, in the known devices, it has been found impossible to detect prevailing faulty operations by a test on the device.

SUMMARY OF THE INVENTION

The main object of the present invention consists in minimizing or eliminating the shortcomings of the known insufflation devices.

Another object of the present invention is to provide an insufflation device in which, apart from causing the expansion of the abdominal cavity, the gas bubble engendered in the abdominal cavity is kept under a constant pressure, even if sudden or constant gas losses occur at a high rate of flow. The device will detect alterations of the pressure balance and assume a condition which precludes any risk to the patient.

The present invention consists in an insufflation device for endoscopic interventions, in which a gas which is introducible into an abdominal cavity is fed to an expansion valve either directly from a gas source or via an intermediate container, the expansion valve being connected by a shut-off valve, a pressure gauge and a flow indicator to a supply or feed pipe being insertable into the body cavity. The flow indicator is connected to a switching valve of the supply pipe by two parallel flow channels with the first channel of the two comprising a shut-off valve and an expansion valve placing the gas pressure at a value above the required pressure in the body cavity and the second channel of the two comprising an expansion valve adjustable to the required pressure in the body cavity, flow sensor means with a connected first pressure pickup and first pressure indicator for determining the flow in the second channel. The feed pipe, after the switching valve, has connected to it a second pressure pickup with a second indicator which is constantly compared with the first indicator. For the purpose of rapid filling the body cavity with gas, the switching valve is in a first position to connect the first flow channel for an initial period and the switching valve is then changed to a second position to be switched over to the second flow channel during which the flow is monitored by the flow sensor means. The switching valve is optionally changed between the first and second positions as a function of the gas flow measured in the second channel.

BRIEF DESCRIPTION OF THE DRAWING

The FIGURE is a synoptic diagram of one embodiment of insufflation device constructed in accordance with the invention.

DESCRIPTION OF THE PREFERRED EMBODIMENTS

In accordance with the illustrated example, gaseous $CO_2$ or $N_2O$ is conducted directly under pressure indication from a gas bottle 1 through and via an expansion valve 2 to a valve 6, either via a direct line 3 or via an intermediate container with a filling level gauge 5. The gas is fed via the valve 6 to an expansion valve 7 and a shut-off valve 8 is then opened, so that the can go to a second expansion valve 9 and then reach a valve 12 via either the direct line 11 or through a restrictor 10. From the valve 12, the gas goes to a flow indicator 13.

According to this embodiment of the invention, and for the purpose of rapid filling of the body cavity, the gas is conducted along a first flow channel I into the abdominal cavity. The first channel I extends from the flow indicator 13 to a valve 14 and an expansion valve 15 and then to a switching valve 18, which discharges into a pipe, line or base 23 which terminates in a cannula 24 for transpiercing an abdominal integument. While doing so, the pressure is adjusted by the expansion valve 15 to a value lying above the desired, required pressure to be adopted in the body cavity to obtain, on the one hand, a high rate of gas flow and, on the other hand, to overcome the throughflow resistance in the hose or pipe 23 and in particular that of the cannula 24.

The rapid filling of the body cavity is, in each case, performed via the first flow channel I for a fixed period of, for example, two seconds, and this pressure is not measured. The valve 18 is then switched from a first position connecting the channel I to the line 23 over to a second position only connecting a second flow channel II to the line 23, so that the gas is then conducted from the flow indicator 13 to an adjustable expansion valve 16, which may, for example, be adjusted by means of a motor 17 to the desired, required pressure to be adopted in the body cavity. From the valve 16, the gas flows on a line through a flow sensor means 25 to the switching valve 18 to be carried by the pipe or hose 23 to the cannula 24 that is inserted into the body cavity. The line between the sensor 25 and the valve 18 has a first pressure pickup 21 connected to a first indicator 22. The switching of the valve 18 between the first and second positions occurs until the flow-rate measured by the flow sensor 25 situated in the flow channel II during the use of the second channel II is either equal to zero or approximately equal to zero. Once the flow rate has reached or has approximately reached the value zero, the valve 18 remains constantly switched to the second position to connect the flow channel II to the hose 23 so that pressure fluctuations caused by small gas losses are prevented effectively by a constant pressure equalization.

However, if more than 0.3 liter of gas per minute still flows through the second flow channel II, this means that the desired, required pressure has not yet been reached in the body cavity. This body cavity pressure measurement is converted by a second pressure pickup 26 into an electrical signal and displayed in an analog or digital manner by a second indicator 27. The valve 18 is then again switched immediately to the first position for the first flow channel I for the predetermined period of two seconds. If no more gas flows to the patient from the expansion valve 16 or rather through the second flow channel II after the valve 18 is again switched over to the channel II, this means that the desired, required pressure in the body cavity has been wholly or almost wholly reached.

The switching of valve 18 is controlled by control means 40 which will hold the valve 18 to a first position for connecting channel I to the pipe 23 for a predetermined time and then changes to a second position to connect the channel II to the pipe. The predetermined time can be established by a timing circuit. The switching from channel II to channel I can be caused by a pulse from the sensor 25.

As already described in the foregoing, the valve 18 then remains switched to the second position and second flow channel II, in which condition gas losses smaller than 0.3 liter/minute are made up continuously. If the pressure drops suddenly as a result of greater gas losses which, for example, are caused by a change of instruments or the like, the valve 18 is immediately switched over to the first position and the first flow channel I so that the body cavity may be filled rapidly until the desired, required is reached again in the body cavity.

When the valve 18 is in the second position to connect the second channel II to the line 23, the pressure in the body cavity, which pressure is preselected by means of the expansion valve 16, is measured by the first pressure pickup 21 of the second flow channel II and supplied as an electrical signal to the first indicator 22, which indicates the value of the pressure in the body cavity in a digital or analog manner.

Thanks to the presence of the two pressure pickups 21, 26, as well as of the indicators 22, 27 post-connected thereto, it is possible to verify the proper operation of the insufflation device, which operation is occurring if identical pressure values are indicated after a specific short period following the closing of the feed pipe 23 and the placing in operation of the insufflation device.

For the purpose of checking on a possible indicator deviation from a desired, required pressure, the insufflation device according to the invention constantly performs a comparison between the two pressure values displayed by the indicators 22 and 27. The device includes an electronic evaluator means or system 28 which triggers a first signal or an alarm, such as 31, if the desired, required pressure is exceeded by 5 mms Hg.

If a preselected limiting value of 30 mms Hg is exceeded, a second alarm or second signal is triggered by the means 28 and the feed pipe 23 and the pump 29, as well as possibly other auxiliary devices coupled to outlets 32, 32' and activated by the electronic evaluator system 28, are put out of action by second signals on the outlets 32, 32'. For example, a valve 19, which is on a line with a restrictor 20 and connected by a line 50 to the outlet 32, can be opened to dump the pressure coming from expansion valve 16 from the channel II. Also, a pressure outlet 30 which is connected by a line 51 to the outlet 32', can be opened to bypass both channels I and II. This condition is displayed by one or both indicators 22, 27. Another infeed of gas into the body cavity may then occur only after elimination or correction of the prevailing fault, wrong operation or faulty handling.

The adjustment of the expansion valve 16 to the required maximum pressure in the body cavity and the measurement of the pressure in the second channel II by means of the pressure pickup 21 and the measurement of the pressure in the body cavity by means of the pressure pickup 26, require a continuous comparison between the two pressure values, so that faults may be detected immediately and eliminated in the manner described.

Although various minor modifications may be suggested by those versed in the art, it should be understood that I wish to embody within the scope of the patent granted hereon all such modifications as reasonably and properly come within the scope of my contribution to the art.

I claim:

1. In an insufflation device for introducing a gas into a body cavity through a feed pipe, said device including a feed pipe, a source of gas being selectively connected to an expansion valve by one of a direct line and a second line having an intermediate container, said expansion valve being connected by a shut-off valve, a pressure regulator and flow indicator to the feed pipe which has an end connected to a cannula insertable into the body cavity, the improvements comprising the flow indicator being connected to two parallel flow channels leading to a switching valve connected to said feed pipe, a first flow channel of the two parallel flow channels having a shut-off valve and an expansion valve means for setting the gas pressure at a value above a desired, required pressure in the body cavity, a second flow channel of the two parallel flow channels having an expansion valve being adjustable to the desired, required pressure of the body cavity, flow sensor means for determining the flow in the second flow channel, a first pressure pickup and a first pressure indicator, said feed pipe downstream of said switching valve being connected to a second pressure pickup with a second pressure indicator, first means for constantly comparing the first and second pressure indicators, said switching valve having control means for changing the switching valve between a first position only connecting the first flow channel to the pipe for an initial time period and a second position only connecting a second flow channel to the pipe, said flow sensor means monitoring the flow in the second flow channel while the switching valve is in the second position and then creating a signal for the control means to change the switching valve back to the first position if the flow in the second flow channel exceeds a predetermined amount.

2. In an insufflation device according to claim 1, wherein said first means includes electronic evaluation means for triggering a first signal when the pressure in the body cavity is exceeded by a specific preselectible value above said desired, required pressure and said electronic evaluation means triggering a second signal for blocking the gas feed into the body cavity when the pressure in the body cavity exceeds a preselected limiting value which is greater than said specific preselectible value.

3. In an insufflation device according to claim 2, wherein said evaluation mans being activated due to preselected limiting value being exceeded to prevent operation of the device until after performing an elimination and correction of the wrong operation, faulty control action and erroneous handling which caused the exceeding of the preselected limiting value.

4. In an insufflation device according to claim 2, wherein said electronic evaluation means has an outlet connected to an auxiliary device, said second signal being applied to the outlet to deactivate the auxiliary device.

5. In an insufflation device according to claim 1, wherein the control means for the switching valve switches the switching valve over to the second position and remains in said second position as long as the flow in the second channel is equal to or approximately equal to zero.

6. In an insufflation device according to claim 5, wherein said first means includes electronic evaluation means for triggering a first signal when the pressure in the body cavity is exceeded by a specific preselected value above said desired, required pressure and said electronic evaluation means triggers a second signal for blocking the gas feed into the body cavity when the pressure in the body cavity exceeds a preselected limiting value greater than said specific preselected value.

7. An insufflation device according to claim 6, wherein said evaluation means maintains the insufflation device in a deactivated condition when the preselectible limiting value has been exceeded until the wrong operation, faulty control action and erroneous handling causing said deactivation has been corrected and eliminated.

* * * * *